(12) United States Patent
MacDonald

(10) Patent No.: US 7,829,345 B1
(45) Date of Patent: Nov. 9, 2010

(54) REMOTE DETECTION OF PEROXIDE COMPOUNDS VIA LASER INDUCED FLUORESCENCE

(75) Inventor: Steven Andrew MacDonald, Arlington, VA (US)

(73) Assignee: ITT Manufacturing Enterprises, Inc., Wilmington, DE (US)

(\*) Notice: Subject to any disclaimer, the term of this patent is extended or adjusted under 35 U.S.C. 154(b) by 0 days.

(21) Appl. No.: 12/329,045

(22) Filed: Dec. 5, 2008

(51) Int. Cl.
*G01N 21/76* (2006.01)
*G01N 21/64* (2006.01)

(52) U.S. Cl. .................. 436/172; 436/135; 436/136; 422/82.08; 422/82.09; 356/301; 356/302; 356/320

(58) Field of Classification Search ................ 436/172, 436/171; 356/51, 300, 301; 73/35.14
See application file for complete search history.

(56) References Cited

U.S. PATENT DOCUMENTS

| | | | |
|---|---|---|---|
| 3,850,525 | A | 11/1974 | Kaye |
| 4,689,052 | A | 8/1987 | Ogren et al. |
| 5,364,795 | A | 11/1994 | Sausa et al. |
| 5,728,584 | A | 3/1998 | Sausa et al. |
| 5,759,859 | A | 6/1998 | Sausa |
| 5,826,214 | A | 10/1998 | Lieb et al. |
| 5,835,649 | A | 11/1998 | Turner et al.. |
| 5,906,946 | A | 5/1999 | Sausa et al. |
| 6,287,869 | B1 | 9/2001 | Hug et al. |
| 6,693,944 | B1 | 2/2004 | Hug et al. |
| 7,088,435 | B2 | 8/2006 | Brestel et al. |
| 7,113,275 | B2 | 9/2006 | Gardner, Jr. et al. |
| 7,245,371 | B2 | 7/2007 | Wang et al. |
| 7,359,040 | B1 | 4/2008 | Pendell-Jones et al. |
| 2002/0109110 | A1 | 8/2002 | Some et al. |
| 2006/0061762 | A1 | 3/2006 | Dwight et al. |

FOREIGN PATENT DOCUMENTS

WO WO 2008/002659 A2 1/2008

OTHER PUBLICATIONS

Matsumi, Y.; Kono, M.; Ichikawa, T.; Takahashi, K.; Kondo, Y.; Laser-Induced Fluorescence Instrument for the Detection of Tropospheric OH Radicals, 2002, Bull. Chem. Soc. Jpn, 75, 711-717.*

(Continued)

*Primary Examiner*—Krishnan S Menon
*Assistant Examiner*—Allison Gionta
(74) *Attorney, Agent, or Firm*—Edell, Shapiro & Finnan, LLC

(57) ABSTRACT

A method for detection of a peroxide-based compound includes directing ultraviolet light from an ultraviolet light source toward a location remote from the ultraviolet light source, where the ultraviolet light induces photodissociation of a peroxide-based compound located at the remote source into hydroxyl radicals and excitation of the hydroxyl radicals to fluoresce, capturing any fluorescence from the remote location that has been induced by the ultraviolet light directed from the ultraviolet light source toward the remote location, and analyzing the fluorescence that has been captured from the remote location to determine the presence of the peroxide-based compound at the remote location. A system for detection of a peroxide-based compound that performs such method steps is also described herein.

10 Claims, 3 Drawing Sheets

OTHER PUBLICATIONS

Committee on the Review of Existing and Potential Standoff Explosives Detection Techniques, Existing and Potential Standoff Explosives Detection Techniques, National Academy of Science, 2004, Chapter 5, pp. 71-96.*

Johansson, O.; Bood, J.; Alden, M.; Lindblad, U.; Detection of Hydrogen Peroxide Using Photofragmentation Laser-Induced Fluorescence, Applied Spectroscopy, vol. 62, No. 1, 2008, Received by the journal on Jun. 29, 2007, p. 66-72.*

Schulte-Ladbeck, R.; Vogel, M.; Karst, U.; Recent Methods for the Determination of Peroxide-Based Explosives, Anal. Bioanal. Chem., 2006, 386, 559-565.*

U.S. Appl. No. 12/125,961.

R Bombach, W. Hubschmid, A. Inauen, B. Kappeli, "Simultaneous Raman and LIF Measurements in a Catalytic Burner," Proceedings 22nd IEA Task Leaders Meeting 2000 on Energy Conservation and Emissions.

S. Hong, J. Birmingham, M. Fountain, "Mesochannel Gas Sampler for Rapid Sample Collection and Concentration," Mar. 2001, pp. 1-15, Prepared for the Department of Energy Under DOE Grant No. DE-FG03-00ER83048 by MesoSystems Technology, Inc. Kennewich, Washington.

Lockheed Martin Maritime Systems & Sensors, "Biological Aerosol Warning System," Cleared for Public Domain Release DoD/00-S-0607, Dec. 1999, Aug. 2003, Manassas, VA.

General Dynamics Armament and Technical Products, "Biological Agent Warning Sensor," 2007, Charlotte, NC.

Rasmus Schulte-Ladbeck, Martin Vogel and Uwe Karst, "Recent Methods for the Determination of Peroxide-Based Explosives," Anal. Bioanal. chem 386: 559-565, (2006).

Rasmus Schulte-Ladbeck, Peter Kolla and Uwe Karst, "Trace Analysis of Peroxide-Based Explosives," Analytical Chemistry, vol. 75, No. 4, pp. 731-735, Feb. 15, 2003.

Jinian Shu, Ilana Bar, Salman Rosenwaks, "Dinitrobenzene Detection by Use of One-Color Laser Photolysis and Laser-Induced Fluorescence of Vibrationally Excited NO," Applied Optics, vol. 38, No. 21, pp. 4705-4710, Jul. 20, 1999.

N. Daugey, J. Shu, I. Bar, S. Rosenwaks, "Nitrobenzene Detection by One-Color Laser-Photolysis/Laser-Induced Fluorescence of NO (v'=0-3)," Applied Spectroscopy, vol. 53, No. 1, pp. 57-64, 1999.

Gary M. Boudreaux, Tracy S. Miller, Amanda J. Kunefke, Jagdish P. Singh, Fang-Yu Yueh, David L. Monts, "Development of a Photofragmentation Laser-Induced-Fluorescence Laser Sensor For Detection of 2,4,6-Trinitrotoluene in Soil and Groundwater," Applied Optics, vol. 38, No. 9, pp. 1411-1417, Mar. 20, 1999.

M. Gaft, L. Nagli, "Standoff Laser Based Spectroscopy for Explosives Detection," Proc. of SPIE vol. 6739, pp. 1-13, 2007.

Dov Heflinger, Talya Arusi-Parpar, Yosef Ron, Raphael Lavi, "Application of a Unique Scheme for Remote Detection of Explosives," Optics Communications, pp. 327-331, Apr. 1, 2002.

O. Johansson, J. Bood, M. Alden, U. Lindblad, "Detection of Hydrogen Peroxide Using Photofragmentation Laser-Induced Fluorescence," Applied Spectroscopy, vol. 62, No. 1, pp. 66-72, Nov. 1, 2008.

Talya Arusi-Parpar, Dov Heflinger, Raphael Lavi, "Photodissociation Followed by Laser-Induced Fluorescence at Atmospheric Pressure and 24 C: A Unique Scheme for Remote Detection of Explosives," Applied Optics, vol. 40, No. 36, pp. 6677-6681, Dec. 20, 2001.

Carol C. Phifer, Randal L. Schmitt, Lawrence R. Thorne, Philip Hargis, Jr., John E. Parmeter, "Studies of the Laser-Induced Fluorescence of Explosives and Explosive Compositions," Sandia Report, Sandia National Laboratories, pp. 1-70, Oct. 2006.

Rosario C. Sausa, Vaidhianat Swayambunathan, Grubax Singh, "Detection of Energetic Materials by Laser Photofragmentation/Fragment Detection and Pyrolysis/Laser-Induced Fluorescence," Army Research Laboratory, Feb. 2001.

Rosario C. Sausa, George W. Lemire, Josef B. Simeonsson, "Sensitive Detection of Gas-Phase Nitro-Containing Energetic Materials Employing 226-nm Radiation," Army Research Laboratory, Jul. 1993.

J. Shu, I. Bar, S. Rosenwaks, "NO And PO Photofragments as Trace Analyte Indicators of Nitrocompounds and Organophosphonates," Applied Physics B, pp. 665-672, 2000.

Dongdong Wu, Jagdish P. Singh, Fang Y. Yueh, David L. Monts, "2,4,6-Trinitrotoluene Detection by Laser-Photofragmentation-Laser-Induced Fluorescence," Applied Optics, vol. 35, No. 21, pp. 3998-4003, Jul. 20, 1996.

C. M. Wynn, S. Palmacci, R. R. Kunz, J. J. Zayhowski, B. Edwards, M. Rothschild, "Experimental Demonstration of Remote Optical Detection of Trace Explosives," Proc. of SPIE vol. 6954, pp. 1-8, 2008.

Klee, Stefan et al., "Doppler Spectroscopy of OH in the Photodissociation of Hydrogen Peroxide", pp. 40-44, J. Chem. Phys., vol. 85, No. 1, Jul. 1986.

Liu, Ya-Jun et al., Theorectical Study of the Photodissociation of Low Lying Excited States of Hydrogen Peroxide, Molecular Physics, Dec. 10-20, 2004, vol. 102, No. 23-24, 2575-2584.

* cited by examiner

REMOTE DETECTION OF PEROXIDE COMPOUNDS VIA LASER INDUCED FLUORESCENCE

FIELD OF THE INVENTION

The invention relates to methods and devices for detecting peroxide compounds, in particular peroxide-based explosive compounds.

BACKGROUND

The use of peroxide based explosives in terrorist and other crime related activities has become of some concern in recent years. In particular, the use of acetone peroxide explosives such as triacetone triperoxide (TATP) has increased over recent years in criminal activities throughout the world.

Triacetone triperoxide can be formed by an acid-catalyzed reaction of hydrogen peroxide with acetone and has the following molecular structure:

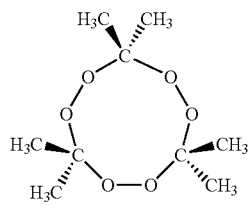

The acetone peroxides such as TATP can detonate when ignited or when confined under certain conditions. Peroxide based explosive materials have recently become popular in criminal activities in part because they are not easily detectable by conventional explosive detection systems and methods, which typically focus upon the detection of nitrogen-containing chemical compounds.

While some methods for detection of TATP are presently available, these methods typically involve wet chemical analysis and expensive, bulky laboratory equipment. It would be desirable to provide a system and method for remote detection and identification of acetone peroxide substances to ensure safety in areas that may be targeted for terrorist or criminal activities (e.g., the airline industry, military zones, etc.).

SUMMARY

A method for detection of a peroxide-based compound comprises directing ultraviolet light from an ultraviolet light source toward a location remote from the ultraviolet light source, where the ultraviolet light induces photodissociation of a peroxide-based compound located at the remote source into hydroxyl radicals and excitation of the hydroxyl radicals to fluoresce, capturing any fluorescence from the remote location that has been induced by the ultraviolet light directed from the ultraviolet light source toward the remote location, and analyzing the fluorescence that has been captured from the remote location to determine the presence of the peroxide-based compound at the remote location.

A system for remote detection of a peroxide-based compound, the system comprising a light source that is configured to generate and direct ultraviolet light toward a location remote from the light source so as to induce photodissociation of a peroxide-based compound located at the remote source into hydroxyl radicals and excitation of the hydroxyl radicals to fluoresce, an optical element system that is configured to capture fluorescence from the remote location as a result of hydroxyl radicals induced by the beam of ultraviolet light, a detector that generates fluorescence spectra from the fluorescence captured by the optical element system, and an analyzer that is configured to analyze the fluorescence spectra generated by the detector so as to determine a presence of the peroxide-based compound at the remote location.

In an example embodiment, the peroxide-based compound detected for the system and method described above comprises triacetone triperoxide (TATP).

The above and still further features and advantages of the present invention will become apparent upon consideration of the following detailed description of specific embodiments thereof.

DETAILED DESCRIPTION

A system and corresponding method for remote detection of a peroxide-based compound, such as triacetone triperoxide (TATP), comprises providing and utilizing equipment that subjects the peroxide compound of interest at a detection surface or area to incident laser light that ultimately generates emitted light, typically referred to as laser-induced fluorescence (or LIF). The cascade of events is as follows: the peroxide compound is first decomposed or photodissociated through one or more steps into hydroxyl radicals, and the hydroxyl radicals are then excited to emit fluorescence which is detected by the system to identify the existence of the peroxide compound.

In the present invention, LIF techniques are preferred over other spectroscopic techniques due to the ability to distinctly identify fragment molecules such as OH radicals from the acetone peroxide compounds being detected. While other techniques, such as Raman spectroscopic techniques, have been shown to provide high specificity in the identification of compounds, detection explosive materials using Raman-based sensors has limited sensitivity due to the weakness of the Raman effect. The weakness of the Raman effect is especially problematic for sensing explosive materials that are present at low concentrations or in the vapor phase, which is the case for TATP and other peroxide-based compounds that readily sublime. In contrast to Raman signals, fluorescence signals are several orders of magnitude stronger, and detection techniques that rely on the generation and capture of fluorescence signals are highly sensitive.

Direct detection of peroxide-based compounds using native fluorescence of the target substance can be difficult because either they do not exhibit fluorescense or because the fluorescence spectra are typically broad and structureless (i.e., no discriminating spectral features). However, selective photofragments obtained from the photodissociation of peroxide-based compounds yield strong fluorescence signals that produce structured fluorescence spectra. In particular, the hydroxyl radical obtained from laser-induced photodissociation of the peroxide-based compound is highly useful as a photofragment for LIF detection. Absorption by the OH radical via its various A-X bands, e.g. (0,0), (1,0), (2,0), (1,1) transitions at or near 309 nm, 283 nm, 262 nm, and 315 nm, results in discrete LIF emissions that can be collected and analyzed. The unique fluorescence spectral fingerprint of the OH radical which has been fragmented from the peroxide-based compound of interest can serve as an indicator for such compound in contrast to attempting to analyze fluorescence profiles of the larger molecule itself, which may have multiple pathways of energy disposal at the excited energy levels.

Additionally, the detection of fluorescence in this particular spectral window serves as indicator that the location under evaluation warrants closer inspection and possibly added safety precautions.

Figure 1:
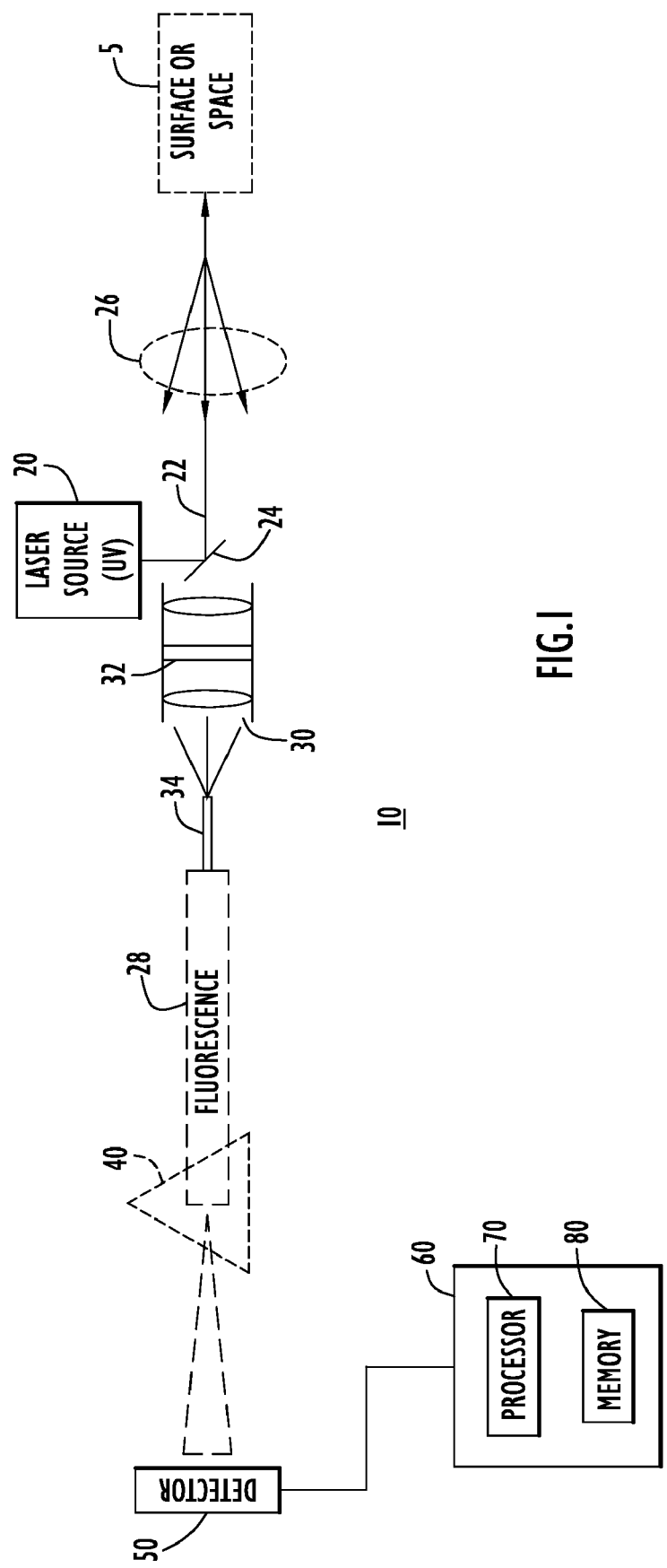
FIG. 1 is a block diagram of an example system for remote detection of the presence of a peroxide based explosive compound using photofragmentation laser-induced fluorescence.

An example of a system for remote detection of peroxide based compounds is depicted in the block diagram shown in FIG. 1. Referring to this figure, a detection system 10 comprises a laser source 20, a collection optics unit 30 including one or more filters (represented in FIG. 1 as element 32), a detector 50 and an analyzer 60 The system can also optionally include a light dispersive element 40 as described in more detail below. The analyzer 60 includes a processor 70 to analyze the spectral data obtained from the detector and, optionally, a memory unit 80 to store measured data and/or other spectral data corresponding with known peroxide-based compounds or molecule fragments of such compounds. The system 10 may be used to detect the presence of a peroxide-containing compound of interest (e.g., TATP) on a surface or within a space shown at reference numeral 5.

The laser source 20 is configured or adapted to produce a beam 22 of ultraviolet (UV) light at a wavelength that will induce photofragmentation of certain molecules. For example, the laser source 20 may be a type that produces a laser beam of UV light at a wavelength in a range from about 250 nm to about 308 nm (e.g., at wavelengths of about 254 nm, about 262 nm, about 266 nm, 282 nm and/or below 308 nm), where the wavelength of the UV light source can be varied during system operation. The laser source can provide a steady and constant beam or, alternatively, a pulsed beam having suitable energy flux to achieve dissociation and fluorescence of the OH radicals. An optical element 24 may also be provided to direct the UV light beam 22 to the surface or space 5.

The collection optics unit 30 captures the fluorescence emissions shown at reference numeral 26 from the surface or space 5. The filter 32 eliminates from the captured fluorescence emissions any energy associated with the laser beam as well as other background or scattered light, substantially reducing the spectral emissions to a range that is associated with OH fluorescence. The filtered LIF emissions 28 are directed from the collection optics to detector 50.

The detector 50 can be a single-channel or multi-channel detector, depending upon the type or types of filter or filters utilized to block scattered light captured by the collection optics unit 30 and the wavelength detection range that is desired. The strongest OH fluorescence generated by the system will be in a range from about 300 nm to 315 nm. In one embodiment, the detector can be configured as a single channel detector that detects fluorescence at 309 nm corresponding with absorption by OH radicals at an A-X band of (0,0). In another embodiment, a multi-channel detector can be provided in the system to detect OH fluorescence at different wavelengths within a selected range (e.g., from about 300 nm to 315 nm).

Optionally, a dispersive element can be provided within the system (e.g., as shown in dashed lines as element 40 in FIG. 1) to disperse and redirect fluorescence light received from the collection optics unit 30 and onto the detector 50. The dispersive element may comprise a diffraction grating that operates across a suitable range (e.g., approximately 15 nm or a wavelength range from about 300 nm to 315 nm). In this optional embodiment, the detector 50 is configured as a multi-channel detector to detect fluorescence over at least a portion of the dispersed wavelength range.

The detector 50 generates fluorescence spectra from the fluorescence light received from the collection optics unit 30 (or, optionally, from the light dispersive element 40). As noted above, the detector is configured to detect light in a range from about 300 nm to about 315 nm or at a specified wavelength such as 309 nm, where OH radicals dissociated from the target peroxide compound of interest have been excited to emit fluorescence upon being subjected to UV light at a wavelength less than 309 nm.

It is noted that the block diagram shown in FIG. 1 is a schematic representation of the system and should in no way be construed as limiting the claimed invention to the specific location of elements shown in this figure. For example, FIG. 1 shows that the laser source 20 is positioned offset from the collection optics unit. However, the laser source 20 can also be positioned directly in front of the collection optics unit 30. In addition, FIG. 1 shows that the filter 32 is positioned within the collection optics unit 30, but the filter 32 may also be positioned downstream of the collection optics unit 30 at the either end of the optical fiber 34.

The analyzer 60 analyzes the fluorescence spectra to determine whether the measured spectral data corresponds with excited OH radicals that have been photodissociated from the peroxide compound of interest at surface or space 5. For example, the processor 70 of analyzer 60 can be configured to execute one or more software programs stored in the memory unit 80 to compare the measured fluorescence spectra against known OH spectra data also stored in the memory unit. Alternatively, the processor may be configured to execute one or more software programs that determine the presence of excited OH radicals by comparison of the measured light intensity at one or more selected wavelengths with threshold intensity values at such wavelengths based upon test conditions. In an example embodiment with a system including a single channel detector that measures fluorescence at 309 nm, the intensity of the measured spectral data at this wavelength can be compared with a threshold or baseline value to determine the presence and/or amount of the peroxide-based compound that is present based upon the difference between the measured intensity value and the baseline value. This same analysis (comparison of measured intensity value with a baseline value) can also be performed at two or more different wavelengths.

Figure 2:
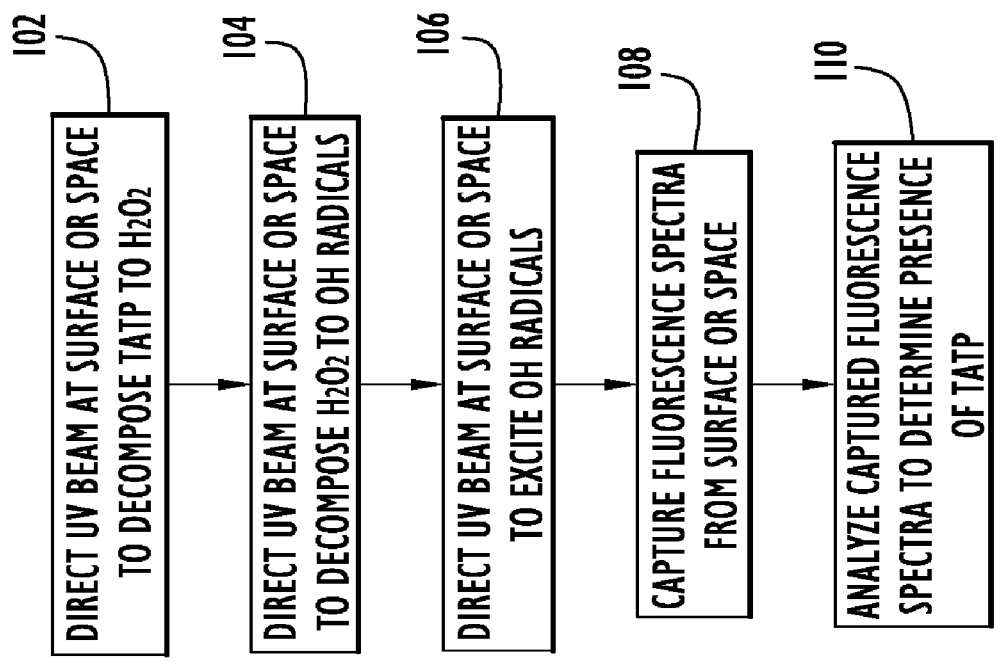
FIG. 2 is a flow chart depicting an example process for remote detection of a peroxide based explosive using photofragmentation laser-induced fluorescence.

The system described above and schematically depicted in FIG. 1 can be utilized for remote detection of an acetone peroxide explosives, in particular, TATP. In an example embodiment, the system is utilized to detect the presence of TATP along a surface or at a particular location utilizing the steps as set forth in the flowchart of FIG. 2. In this example, a pulse of a UV beam is directed by the laser source 20 toward the detection surface or space 5 and at a first wavelength (e.g., about 254 nm) to achieve photdissociation or decomposition of TATP into fragments including hydrogen peroxide ($H_2O_2$) (Step 102). Next, the laser source 20 directs a UV beam pulse at a second wavelength (e.g., about 266 nm) toward the detection surface or space 5 to achieve photolysis of $H_2O_2$ into OH radicals (Step 104). The laser source 20 directs a third UV beam pulse at an appropriate wavelength (e.g., a wavelength that is no greater than about 309 nm, such as 282 nm) to excite the OH radicals so as fluoresce (Step 106). The laser induced fluorescence (LIF) of the OH radicals is captured and filtered by the collection optics unit 30 (and, optionally, dispersed by light dispersive element 40) prior to being sent to the detector 50 (Step 108). The analyzer 60 receives the spectral data from the detector 50 to identify the fluorescence spectra and provide an indication of the presence and/or concentration or amount of TATP at the surface or space 5 (Step 110).

While the method described above utilizes three steps for directing a UV beam containing different wavelengths to induce the complete cascade of events (namely, dissociation of TATP into OH radicals followed by photoexcitation of OH radicals), it may be possible in certain applications to provide a UV light beam at a single wavelength or at two separate wavelengths to facilitate both photodissociation of the target peroxide-based compound as well as inducing LIF of the photofragments.

The system and method described above is useful in particular for a variety of applications involving remote or stand-off detection of explosive peroxide compounds such as TATP. For example, the system and method described above can be used for detection of explosive peroxide-based materials in solid, liquid or gas phase in any environment including, without limitation, civilian environments (e.g., airports, postal packages, etc.) and battlefield environments (e.g., war zones, border patrols, etc.). In addition, the system and method can further be utilized for detection and quantifying a concentration or amount of the peroxide-based compound based upon the measured intensity of the captured fluorescence corresponding with the excited OH radicals.

Figure 3:
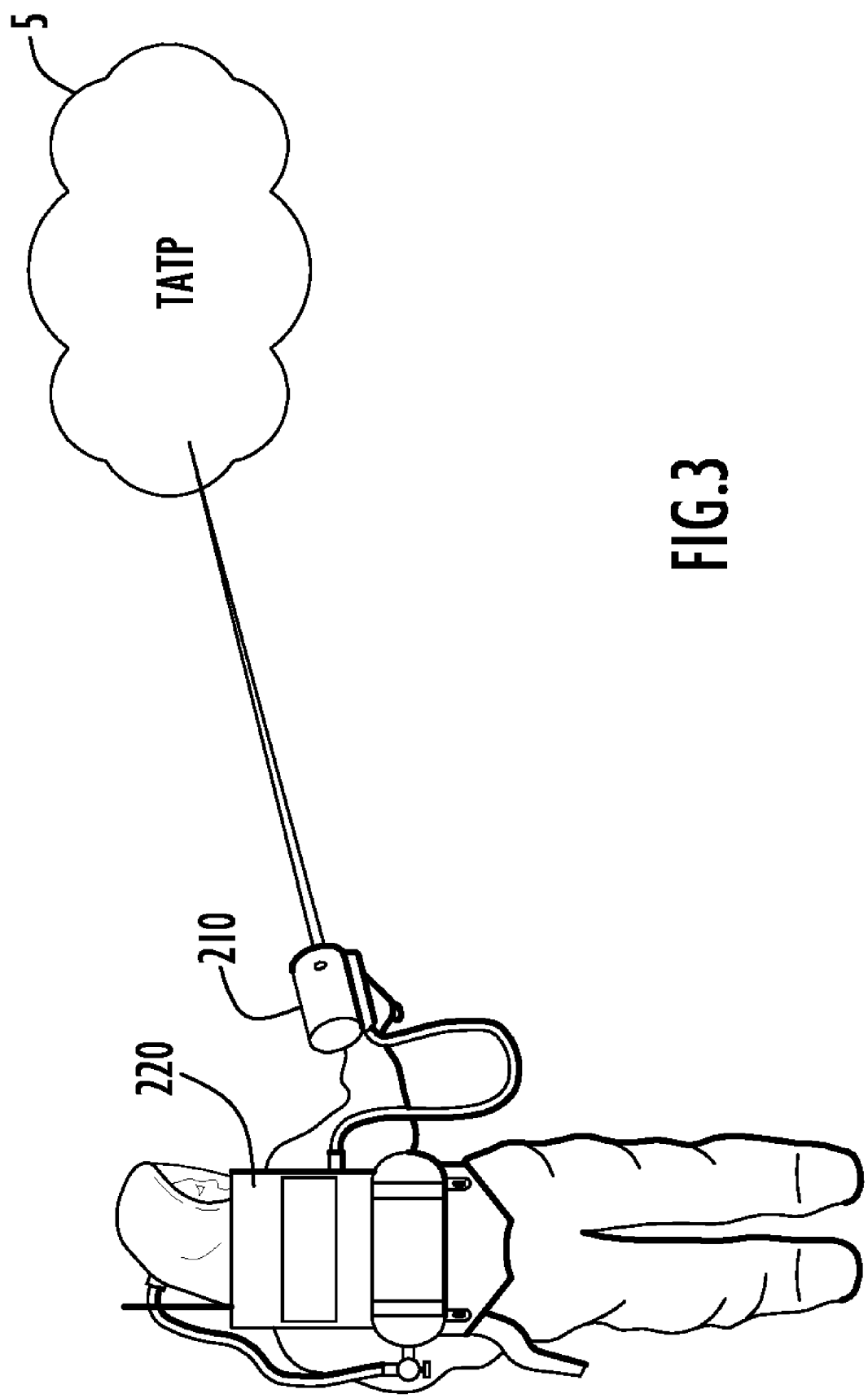
FIG. 3 is an example remote detection device for use by a person which incorporates the system of FIG. 1.

Point detection of peroxide-based explosive materials can be achieved at remote or standoff distances with a hand-held or vehicle-mounted detector so as to provide "on the move" detection capabilities. In an example embodiment shown in FIG. 3, a hand-held portable unit is shown including scanning gun 210 that is held by the user, which includes the laser source and at least a portion of the optics required to capture fluorescence, and also a pack 220 (shown in FIG. 3 as a backpack unit strapped to the user) that includes other portions of the system (e.g., the detector and analyzer). As can be seen in FIG. 3, the user aims the scanning gun 210 toward a location 5 of interest and activates the laser source to generate a laser beam for performing the steps of photodissociation of any peroxide-based compound (e.g., TATP) which may be at such location and exciting OH radicals for LIF detection. This allows the user to determine the presence and/or concentration of a peroxide-based compound at the location of interest while maintaining a safe distance from the location.

The system can also be further miniaturized such that all of the system components are housed within a single, handheld unit (i.e., so as to eliminate the backpack unit described above and shown in FIG. 3). Such a system provides useful storage and transport of the device by a user in "on the move" applications.

The system can include any suitable audio and/or visual indicator which provides an indication regarding the presence and/or amount of the peroxide-based compound at the particular location being tested. For example, the system can include an audio alarm that indicates the presence of TATP or other peroxide-based compound upon detection of such compound. The system can also include an LED indicator and/or a display screen to visually indicate the presence of TATP or other peroxide-based compound. The system can further include an input device such as a keypad combined with a visual display, where the keypad facilitates user input commands to control processor functions such as display and saving of measured spectral data as well as other functions for controlling system operation and analysis of the measured spectral data.

The system described above can be configured so as to be capable of remotely detecting the presence and concentration of peroxide-based compounds from distances of as much as 5 meters, 10 meters or greater and with concentrations of such compounds at the remote location in amounts as low as 1 ppm or less. The system is further configured to provide an indication of the presence of a peroxide-based compound in less than 5 seconds from the time at which the initial beam of UV light is projected toward the location being tested. In addition, the system provides remote detection of peroxide-based compounds, such as TATP, in the solid, liquid and vapor phases utilizing easy-to-use mobile equipment without the requirement of wet chemistry analysis techniques or the consumption of any compound or material during the detection analysis.

Having described example system and method embodiments of remotely detecting peroxide-based compounds, variations and changes will be suggested to those skilled in the art in view of the teachings set forth herein. It is therefore to be understood that all such variations, modifications and changes are believed to fall within the scope of the present invention as defined by the appended claims.

What is claimed:

1. A method for detection of a peroxide-based compound, the method comprising:
   directing ultraviolet light from an ultraviolet light source toward a location remote from the ultraviolet light source including the following steps:
   directing a first beam of ultraviolet light at a first wavelength to induce photodissociation of the peroxide-based compound into fragments including hydrogen peroxide;
   directing a second beam of ultraviolet light at a second wavelength to induce photolysis of hydrogen peroxide to hydroxyl radicals; and
   directing a third beam of ultraviolet light at a third wavelength to excite the hydroxyl radicals so as to emit fluorescence;
   capturing any fluorescence from the remote location that has been emitted by the excited hydroxyl radicals; and
   analyzing the fluorescence that has been captured from the remote location to determine the presence of the peroxide-based compound at the remote location.

2. The method of claim 1, wherein the first wavelength is about 254 nm.

3. The method of claim 1, wherein the second wavelength is about 266 nm.

4. The method of claim 3, wherein the third wavelength is no greater than about 309 nm.

5. The method of claim 1, wherein the peroxide-based compound comprises triacetone triperoxide (TATP).

6. The method of claim 1, wherein the ultraviolet light source is separated from the remote location at a distance of at least about 5 meters.

7. The method of claim 1, wherein the concentration of the peroxide-based compound at the remote location is no greater than about 1 ppm.

8. The method of claim 1, wherein the method is performed utilizing a hand-held portable unit including an ultraviolet light source configured to be held in the hand of a user such that the user can aim the ultraviolet light source toward the remote location for directing beams of light toward the remote location.

9. The method of claim 8, wherein the unit further comprises a detector portion separate from the ultraviolet light source that is configured for support by a user and includes at least an analyzer to analyze the fluorescence that has been captured from the remote location so as to determine the presence of the peroxide-based compound at the remote location.

10. The method of claim 9, wherein the detector portion is configured as a backpack unit to be strapped to the user.

* * * * *